(12) United States Patent
Dyke et al.

(10) Patent No.: US 6,353,010 B1
(45) Date of Patent: Mar. 5, 2002

(54) BICYCLIC ARYL CARBOXAMIDES AND THEIR THERAPEUTIC USE

(75) Inventors: Hazel Joan Dyke; John Gary Montana, both of Cambridge (GB)

(73) Assignee: Darwin Discovery, Ltd. (GB)

( * ) Notice: Subject to any disclaimer, the term of this patent is extended or adjusted under 35 U.S.C. 154(b) by 0 days.

(21) Appl. No.: 09/422,473

(22) Filed: Oct. 21, 1999

Related U.S. Application Data

(63) Continuation of application No. 08/971,806, filed on Nov. 17, 1997, now abandoned.

(30) Foreign Application Priority Data

Nov. 15, 1996 (GB) ................................................ 9623860
Apr. 22, 1997 (GB) ................................................ 9708062

(51) Int. Cl.[7] ........................ A61K 31/50; A01N 43/40; C07D 241/36; C07D 409/00; C07D 263/52
(52) U.S. Cl. ........................ 514/367; 514/249; 514/321; 514/324; 514/375; 514/394; 544/353; 544/354; 544/355; 546/197; 546/200; 546/202; 548/14; 548/152; 548/217; 548/304.7; 548/357
(58) Field of Search ................................ 514/367, 375, 514/249, 394, 321, 324; 544/353, 354, 355; 548/152, 217, 304.7, 357, 14; 546/197, 200, 202

(56) References Cited

U.S. PATENT DOCUMENTS

| | | | | |
|---|---|---|---|---|
| 4,959,379 A | * | 9/1990 | Wagner et al. | 514/367 |
| 5,665,737 A | | 9/1997 | Cavalia et al. | 514/338 |
| 5,705,509 A | | 1/1998 | Gaster et al. | 514/322 |

FOREIGN PATENT DOCUMENTS

| | | |
|---|---|---|
| DE | 4237617 | 5/1994 |
| EP | 0116938 | 2/1984 |
| EP | 0456067 | 4/1991 |
| JP | 140442 | 11/1975 |
| WO | 9406782 | 3/1994 |
| WO | 9406783 | 3/1994 |
| WO | 9408962 | 3/1994 |
| WO | 9422839 | 10/1994 |
| WO | 9604251 | 2/1996 |
| WO | 9611917 | 4/1996 |

OTHER PUBLICATIONS

Musser, John H. et al. "Synthesis and Antilipolytic Activities of Quinolyl Carbanilates and Related Analogues" J. Med. Chem. 30:62–67, 1987.

Nuhrich, A. et al. "Synthesis and Inhibitory Effects on Platelet Aggregation of 3–(2–thienyl)–and 3–(1–imidazolyl)–1,2–benzisoxazole Derivatives" Eur. J. Med. Chem. 29–75–83, 1994.

Kodama et al. (1976) "Benzothiazole Derivatives" Chemical Abstracts 85(3):691, abstract No. 21335h.

* cited by examiner

Primary Examiner—Richard L. Raymond
Assistant Examiner—Tamthom Truong
(74) Attorney, Agent, or Firm—Saliwanchik, Lloyd & Saliwanchik

(57) ABSTRACT

Compounds of the formula (i)

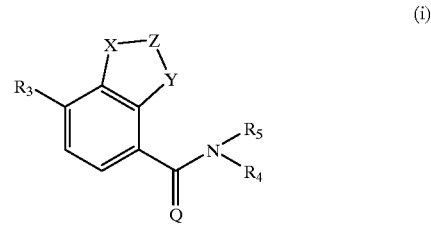

have therapeutic utility via inhibition of TNF or phosphodiesterase.

18 Claims, No Drawings

BICYCLIC ARYL CARBOXAMIDES AND THEIR THERAPEUTIC USE

This application is a continuation of application U.S. Ser. No. 08/971,806, filed Nov. 17, 1997, now abandoned.

FIELD OF THE INVENTION

The present invention relates to novel heterocyclic compounds and pharmaceutically-acceptable salts thereof, processes for their production and formulation and use as pharmaceuticals.

BACKGROUND OF THE INVENTION

2-Thienylbenzoxazoles with anti-aggregating activity are described in *Eur. J. Med. Chem.* (1994) 29:75.

EP-A-0116938 and *J. Med. Chem.* (1987) 30 62 describe heteroaryloxycarboxamides as lipolysis inhibitors useful in the treatment of ischemic heart disease and hypertriglyceridemia.

WO-A-9406783 and WO-A-9406782 describe heteroarylsulphonamides having insecticidal, nematicidal, acaricidal and fungicidal activity.

WO-A-9604251 describes aryloxy derivatives of heteroaryl compounds as bradykinin inhibitors.

Heteroaryl compounds are described as fibrinogen antagonists in WO-A-9408962.

EP-A-0498722 describes amide derivatives of heteroaryl compounds.

Quinoxalines are disclosed as performance enhancers for animals in EP-A-0456067.

Benzimidazoles are described as dopamine antagonists in WO-A-9422839.

DE-A-4237617 discloses imidazoles as antiparasitic agents.

Phosphodiesterases (PDE) and Tumour Necrosis Factor (TNF), their modes of action and the therapeutic utilities of inhibitors thereof, are described in WO-A-9720833 and PCT/GB97/01361, the contents of which are incorporated herein by reference. The same documents disclose carboxamides having utility as PDE and TNF inhibitors.

SUMMARY OF THE INVENTION

This invention is directed to the pharmaceutical use of a compound of formula (i) below to treat disease states, for example disease states associated with proteins which mediate cellular activity, for example by inhibiting tumour necrosis factor and/or by inhibiting phosphodiesterase IV. According to the invention, novel compounds are of formula (i):

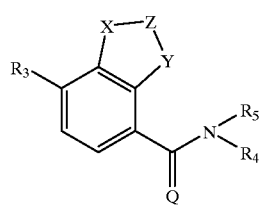

(i)

wherein (1) X is N and (a) Z is $=CR_1-CR_2=$ and Y is N, (b) Z is $=CR_1-$ and Y is O, S or $NR_4$, or (c) Z is $=CR_1-N=$ and Y is $CR^2$, or (2) X is $NR_4$, Z is $-CR_1=$ and Y is N;

Q is O or S;

$R_1$ and $R_2$ are the same or different and are each $COR_6$, $C(=NOR_6)R_{13}$, alkyl-$C(=NOR_6)R_{13}$, $NR_8R_9$, $CON(R_6)_2$, halogen, $CF_3$, CN, $CO_2H$, $CO_2R_{10}$, $R_6$, CO-het where het is a heterocyclic ring (such as morpholine or piperidine) attached via a N atom in the ring and optionally substituted with one or more $R_{14}$, or

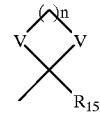

$R_3$ is OH, thioalkyl, or $C_{1-4}$ alkoxy or cycloalkoxy each optionally substituted with one or more halogens, $R_4$ is H or alkyl;

$R_5$ is aryl or heteroaryl, either of which may be optionally substituted with one or more substitutents chosen from halogen, optionally halogen-substituted alkyl, hydroxy, optionally halogen-substituted alkoxy, $CO_2H$, $CO_2R_{10}$, $CONR_{11}R_{12}$, $COR_{10}$, $SO_2R_{10}$, $SO_2NR_{11}R_{12}$, $NR_8R_9$ and CN;

each $R_6$ is independently H or a group selected from alkyl, cycloalkyl, aryl, heteroaryl, heterocyclo, arylalkl, heteroarylalkyl and heterocycloalkyl, any of which groups is optionally substituted at any position with $R_7$;

$R_7$ is alkyl, hydroxy, $OR_{10}$, $NR_8R_9$, CN, $CO_2H$, $CO_2R_{10}$, $CONR_{11}R_{12}$ or $COR_{10}$, $R_8$ is H, alkyl, cycloalkyl, aryl, heteroaryl, heterocyclo, arylalkyl, heteroarylalkly, heterocycloalkyl, alkylcarbonyl, alkoxycarbonyl, arylcarbonyl, heteroarylcarbonyl, heterocyclocarbonyl, alkylsulphonyl, arylsulphonyl, heteroarylsulphonyl or heterocyclosulphonyl, R, is H, alkyl, cycloalkyl, aryl, heteroaryl, heterocyclo, aralkyl, heteroarylalkyl or heterocycloalkyl; or $NR_8R_9$ is a heterocyclic ring (such as morpholine or piperidine) optionally substituted with $R_{14}$;

$R_{10}$ is alkyl cycloalkyl, aryl, heteroaryl, heterocyclo, arylalkyl, heteroarylalkyl or heterocycloalkyl;

$R_{13}$ and $R_{12}$ are the same or different and are each H or $R_{10}$;

$R_{13}$ is $R_{10}$ optionally substituted with one or more $R_7$;

$R_{14}$ is alkyl, arylalkyl or heteroarylalkyl; and $R_{15}$ is alkyl, V is O or S, and n is 2–4; and pharmaceutically-acceptable salts thereof.

Compounds of the invention have a bicyclic aryl nucleus. Depending on the definitions of X, Y, and Z, they are (1a) quinoxalines, (1b) benzoxazole; benzthiazoles or benzimidazoles, (1c) quinazolines or (2) benzimidazoles (differently substituted from those under 1b). Preferred compounds are defined in the subclaims.

DESCRIPTION OF THE INVENTION

Suitable pharmaceutically-acceptable salts are pharmaceutically-acceptable base salts and pharmaceutically-acceptable acid addition salts. Certain of the compounds of formula (i) which contain an acidic group form base salts. Suitable pharmaceutically-acceptable base salts include metal salts, such as alkali metal salts for example sodium salts, or organic amine salts such as that provided with ethylenediamine.

Certain of the compounds of formula (i) which contain an amino group from acid addition salts. Suitable acid addition salts include pharmaceutically-acceptable inorganic salts such as the sulphate, nitrate, phosphate, borate, hydrochloride and hydrobromide and pharmaceutically-acceptable organic acid addition salts such as acetate, tartrate, maleate, citrate, succinate, benzoate, ascorbate, methane-sulphate, α-ketoglutarate, αglycerophosphate and glucose-1-phosphate. The pharmaceutically-acceptable salts of the compounds of formula (i) are prepared using conventional procedures.

It will be appreciated by those skilled in the art that some of the compounds of formula (i) may exist in more than one tautomeric form. This invention extends to all tautomeric forms. It will be appreciated that the compounds according to the invention can contain one or more asymmetrically substituted carbon atoms. The presence of one or more of these asymmetric centers in a compound of formula (i) can give rise to stereoisomers, and in each case the invention is to be understood to extend to all such stereoisomers, including enantiomers, and diastereoisomers and mixtures including racemic mixtures thereof.

When used herein the term alkyl whether used alone or when used as a part of another group includes straight and branched chain alkyl groups containing up to 6 atoms. Alkoxy means an alkyl-O-group in which the alkyl group is as previously described. Cycloalkyl includes a non-aromatic cyclic or multicyclic ring system of about 3 to 10 carbon atoms. The cyclic alkyl may optionally be partially unsaturated. Cycloalkoxy means a cycloalkyl-I-group in which cycloalkyl is as defined above. Aryl indicates an aromatic monocyclic or multicyclic carbocyclic group containing about 6 to 10 carbon atoms. Arylalkyl means an aryl-alkyl-group wherein the aryl and alkyl are as described herein. Heteroarylalkyl means a heteroaryl-alkyl group and heterocycloalkyl means a heterocyclo-alkyl group. Alkylcarbonyl means an alkyl-CO-group in which the alkyl group is as previously described. Arylcarbonyl means an aryl-CO-group in which the aryl group is as previously described. Heteroarylcarbonyl means a heteroaryl-CO-group and heterocyclocarbonyl means a heterocyclo-CO-group. Arylsulphonyl means an aryl-$SO_2$-group in which the aryl group is as previously described. Heteroarylsulphonyl means a heteroaryl-$SO_2$-group and heterocyclosulphonyl means a heterocyclo-$SO_2$-group. Alkoxycarbonyl means an alkyloxy-CO-group in which the alkoxy group is as previously described. Alkylsulphonyl means an alkyl-$SO_2$-group in which the alkyl group is as previously described. Heterocyclic ring means about a 5 to about a 10 membered monocyclic or multicyclic ring system (which may saturated or partially unsaturated) wherein one or more of the atoms in the ring system is an element other than carbon chosen from amongst nitrogen, oxygen or sulphur atoms. Heteroaryl means about a 5 to about a 10 membered aromatic monocyclic or multicyclic hydrocarbon ring system in which one or more of the atoms in the ring system is an element other than carbon, chosen from amongst nitrogen, oxygen or sulphur, if desired, a N atom may be in the form of an N-oxide. Heterocyclo means about a 5 to about a 10 membered saturated or partially saturated monocyclic or multicyclic hydrocarbon ring system in which one or more of the atoms in the ring system is an element other than carbon, chosen from amongst nitrogen, oxygen or sulphur. Halogen means fluorine, chlorine, bromine or iodine.

"TNF mediated disease or disease states" means any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically delineated otherwise.

This invention relates to a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (i) or a pharmaceutically-acceptable salt thereof.

PDE IV inhibitors are useful in the treatment of a variety of allergic and inflammatory diseases, including asthma, chronic bronchitis, chronic obstructive airways disease, chronic pulmonary inflammatory disease, atopic dermatitis, atopic eczema, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, ulcerative coritis Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia. PDE IV inhibitors are also useful in conditions ameliorated by neuroprotectant activity, such as cardiac arrest, stroke and intermittent claudication. Additionally, PDE TV inhibitors could have utility as gastroprotectants. A preferred embodiment of the therapeutic methods of the present invention is the treatment of asthma.

The viruses contemplated for treatment herein are those that produce TNF as a result of infection, or those which are sensitive to inhibitions such as by decreased replication, directly or indirectly, by the TNF inhibitors of Formula (i). Such viruses include, but are not limited to HIV-1, HIV-2 and HIV-3, cytomegalovirus (CMV), influenza, adenovirus and the Herpes group of viruses, such as, but not limited to, *Herpes zoster* and *Herpes simplex*.

This invention more specifically relates to a method of treating a mammal, afflicted with a human immunodeficiency virus (HIV), which comprises administering to such mammal an effective TNF inhibiting amount of a compound of Formula (i) or a pharmaceutically-acceptable salt thereof.

The compounds of this invention may be also be used in association with the veterinary treatment or animals, other than humans, in need of inhibition of TNF production. TNF mediated diseases for treatment, therapeutically or prophylactically, in animals include disease such as those noted above, but in particular viral infections. Examples of such viruses include, but are not limited to feline immunodeficiency virus (FIV) or other retroviral infection such as equine infectious anaemia virus, caprine arthritis virus, visna virus, maedi virus and other lentiviruses.

The compounds of this invention are also useful in treating parasites, yeast and fungal infections, where such yeast and fungi are sensitive to upregulation by TNF or will elicit TNF production in vivo. A preferred disease state for treatment is fungal meningitis.

The compounds of formula (i) preferably in pharmaceutically-acceptable form. By pharmaceutically-acceptable form is meant, inter alia, of a pharmaceutically-acceptable level of purity excluding normal pharmaceutical additives such as diluents and carriers, and including no material considered toxic at normal dosage levels. A pharmaceutically-acceptable level of purity will generally be at least 50% excluding normal pharmaceutical additives, preferably 75%, more preferably 90% and still more preferably 95%.

The invention further provides a process for the preparation of a compound of formula (i), in which $R_1$–$R_{15}$ and Q, X, Y and Z are as defined above. It will be appreciated that functional groups such as amino, hydroxyl or carboxyl groups present in the various compounds described below, and which it is desired to retain, may need to be in protected forms before any reaction is initiated. In such instances, removal of the protecting group may be the final step in a particular reaction. Suitable protecting groups for such functionality will be apparent to those skilled in the art. For specific details, see Protective Groups in Organic Synthesis, Wiley Interscience, T W Greene. Thus a process for preparing compounds of formula (i) in which $R_1$ contains an —OH comprises deprotecting (for example by hydrogenolysis or hydrolysis) a compound of formula (i) in which $R_3$ contains an appropriate —OP wherein P represents a suitable protecting group (eg benzyl).

A process for the preparation of a compound of formula (i) comprises reaction of an appropriate carboxylic acid of formula (ii) with a suitable amine of formula (iii)

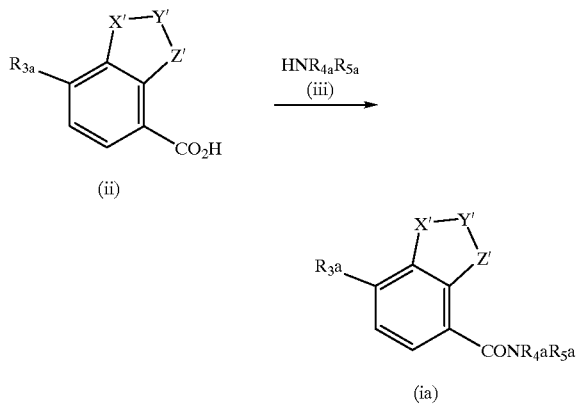

wherein $R_{3a}$ represents $R_3$ as defined in relation to formula (i) or a group convertable to $R_3$ and $R_{4a}$ and $R_{5a}$, similarly represent $R_4$ and $R_5$ or groups convertable to $R_4$ and $R_5$ respectively and X', Y' and Z' represent X, Y and Z or groups convertable to X, Y and Z respectively; and thereafter, if required, converting any group $R_{3a}$ to $R_3$ and/or $R_{4a}$ to $R_4$ and/or $R_{5a}$ to $R_5$ and/or X' to X and/or Y' to Y and/or Z' to Z. The reaction of a carboxylic acid of formula (ii) with an amine of formula (iii) may be carried out under any suitable conditions known to those skilled in the art. Preferably, the carboxylic acid is converted into an acid chloride, mixed anhydride or other activated intermediate prior to reaction with an amine of formula (iii). Preferably, the reaction with the amine of formula (iii) is carried out in the presence of a suitable base, for example an amine base such as triethylamine, preferably in an appropriate solvent such as dichloromethane. In some cases a stronger base, such as sodium hydride, and a polar solvent such as dimethylformamide, will be required.

Carboxylic acids of formula (ii) are either commercially available, previously described compounds or are prepared using standard conditions known to those skilled in the art. For example, a carboxylic acid of formula (ii) is conveniently prepared from a compound of formula (iv), either by formylation to provide an aldehyde of formula (v) followed by oxidation to provide the acid of formula (ii), or by bromination to provide bromide of formula (vi) followed by carboxylation to provide an acid of formula (ii).

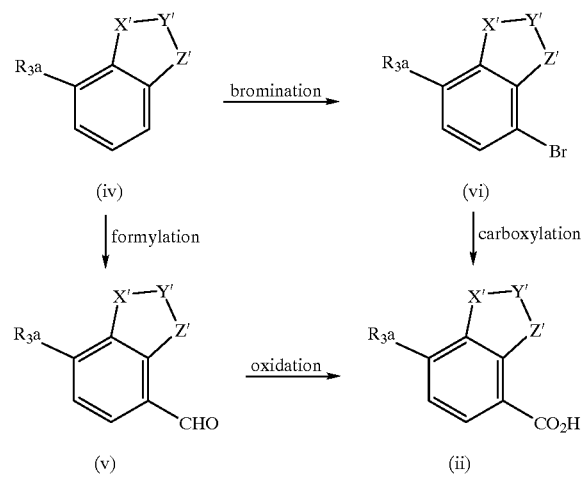

Formylation of a compound of formula (iv) may be carried out under standard conditions known to those skilled in the arts for example by using phosphorous oxychloride and dimethylformamide at elevated temperature. Oxidation of an aldehyde of formula (v) may be carried out using appropriate conditions known to those skilled in the art, for example by using sodium chlorite and sodium phosphate in water/t-butanol in the presence of an acid scavenger such as 2-methyl-2-butene. Bromination of a compound of formula (iv) can be carried out using standard conditions, for example by using bromine in an appropriate solvent such as methanol. Carboxylation of a bromide of formula (vi) can conviently be achieved by the use of an organometal catalyst, such as a palladium catalyst in the presence of an appropriate base in a suitable solvent.

A compound of formula (iv) may be commercially available, a previously described compound or may be prepared using standard conditions known to those skilled in the art. For example, procedures are described in EP-A-0701907, EP-A-0116938, DE-A-4237417, *J. Med. Chem.* (1987) 30 62, *J. Chem. Soc. Perkin Trans. I* (1982) 357 and *J. Chem. Soc. Perkin Trans. I* (1949) 3012, J. Chem. Soc. (1928) 2393 and J. Chem. Soc. (1964) 4645.

Amines of formula (iii) are either commercially available, previously described compounds or are prepared using standard conditions known to those skilled in the art.

A compound of formula (i) may also be prepared by interconversion of other compounds of formula (i). For example, a compound in which $R_1$ contains an alcohol function maybe prepared by reduction of a compound of formula (i) in which $R_1$ contains a carbonyl function.

By way of further example, compounds in which $R_1$ and/or $R_2$ contains an oxime may be prepared from compounds in which $R_1$ and/or $R_2$ contain a carbonyl group. This transformation may be carried out using any appropriate standard conditions known to those skilled in the art. Compounds of formula (i) in which $R_1$ and/or $R_2$ contain a carbonyl group may be reduced using standard conditions known to those skilled in the art (for example with sodium borohydride in an appropriate solvent) to provide compounds in which $R_1$ and/or $R_2$ contains an alcohol group. Compounds in which $R_1$ and/or $R_2$ is alkyl may be prepared by reduction of compounds in which $R_1$ and/or $R_2$ is CO-alkyl using standard conditions known to those skilled in the art (for example hydrazine hydrate in the presence of a suitable base in an appropriate solvent). Other transformations may be carried out on compounds of formula (i) in which $R_1$ and/or $R_2$ contains a carbonyl group. Such transformations include, but are not limited to, reductive amination and alkylation. Any of the above transformations may be carried out either at the end of the synthesis or on an appropriate intermediate. Compounds of formula (i) in which Z is CS may be prepared from compounds of formula (i) in which Z is CO using any appropriate conditions known to those skilled in the art, for example by using Lawesson's reagent.

It will be appreciated that where a particular stereoisomer of formula (i) is required, this may be obtained by conventional resolution techniques such as high performance liquid chromatography or the synthetic processes herein described may by performed using the appropriate homochiral starting material.

A compound of formula (i) or where appropriate a pharmaceutically-acceptable salt thereof and/or a pharmaceutically-acceptable solvate thereof, may be administered per se or, preferably, as a pharmaceutical composition also comprising a pharmaceutically-acceptable carrier.

Accordingly, the present invention provides a pharmaceutical composition comprising a compound of formula (i) or where appropriate a pharmaceutically-acceptable salt thereof and/or a pharmaceutically-acceptable solvate thereof, and a pharmaceutically-acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrasternal injection or infusion tecniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers for example microcrystalline cellulose, lactose, sugar, maize-starch, calcium phosphate, sorbitol or glycine; tabletting lubricants, for example magnesium stearate; disintegrants, for example starch, polyvinylpyrrolidone, sodium starch glycolate or microcrystalline cellulose; or pharmaceutically-acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia, non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 microns, such as from 0.1 to 50 microns, preferably less than 10 microns, for example from 1 to 10 microns, 1 to 5 microns or from 2 to 5 microns. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilised before filling into a suitable vial or ampoule and sealing.

Advantageously, adjuvants such as local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (i), or if appropriate a pharmaceutically-acceptable salt thereof and/or a pharmaceutically-acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or if appropriate a pharmaceutically-acceptable salt thereof are conventional formulations well known in the art, for example, as described in standard text books such as Harry's Cosmeticology published by Leonard Hill Books, Remington's Pharmaceutical Sciences, and the British and U.S. Pharmacopoeias.

Suitably, the compound of formula (i), or if appropriate a pharmaceutically-acceptable salt thereof will comprise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day, and such therapy may extend for a number of weeks or months.

When used herein the term "pharmaceutically-acceptable" encompasses materials suitable for both human and veterinary use.

The following Examples illustrate the invention.

INTERMEDIATE 1

2-Amino-3-nitroanisole

Tetrabutylammonium iodide (0.4 g), sodium hydroxide (4.0 g) in water (40 ml) and iodomethane (3.4 ml) were added to 2-amino-3-nitrophenol (4.0 g) dissolved in tetrahydrofuran (80 ml) at ambient temperature. This mixture was stirred overnight then concentrated in vacuo. After pouring into water (200 ml) it was extracted into ethyl acetate (2×200 ml) then washed with aqueous sodium bicarbonate (100 ml) and saturated brine (100 ml). The solution was dried over anhydrous magnesium sulphate, filtered and evaporated in vacuo to afford the title compound as a dark solid (4.4 g).

TLC $R_f$ 0.7 (50% ethyl acetate in hexane)

INTERMEDIATE 2

2,3-Diaminoanisole

2-Amino-3-nitroanisole (4.3 g) was hydrogenated in ethyl acetate (200 ml) using catalytic 10% palladium on charcoal under an atmosphere of hydrogen at ambient temperature. Once complete the reaction mixture was filtered through Celite and the filtrate evaporated in vacuo to afford the title compound as a brown liquid (3.60 g).

TLC $R_f$ 0.65 (ethyl acetate)

INTERMEDIATE 3

5-Methoxyquinoxaline

Glyoxal sodium bisulphite hydrate (10.0 g) in water (80 ml) was warmed to 60° C. then a solution of 2,3-diaminoanisole (3.40 g) in ethanol (40 ml) was added. The stirred mixture was then heated to 80° C. for 1 h before addition of concentrated hydrochloric acid (6 drops). Heating was continued for 1 h. It was allowed to cool overnight, concentrated in vacuo and poured into aqueous potassium carbonate (40 ml). Ethyl acetate (3×100 ml) extracts were washed with water (100 ml) and saturated brine (50 ml) then dried over anhydrous magnesium sulphate, filtered and evaporated in vacuo to afford the title compound as a yellow solid (3.07 g).

TLC $R_f$ 0.40 (ethyl acetate)

INTERMEDIATE 4

8-Methoxyquinoxaline-5-carboxylic acid

A solution of bromine (0.76 ml) in methanol (10 ml) was added over 15 minutes to 5-methoxyquinoxaline (2.3 g) in methanol (50 ml) at −20° C. under an inert atmosphere. After stirring for 4 h the reaction mixture was stored at −20° C. overnight. It was poured into aqueous sodium metabisulphite (100 ml), basified with sodium bicarbonate and extracted into ethyl acetate (3×100 ml). These extracts were washed with water (100 ml) and saturated brine (50 ml) then dried over anhydrous magnesium sulphate, filtered and evaporated in vacuo to afford a brown solid (2.45 g). Purification by column chromatography using 50% ethyl acetate in hexane as eluent yielded an off-white solid (0.46 g) as a mixture of the 5-bromo and 5,6-dibrominated products. This solid, triphenylphosphine (0.5 g), bis(triphenylphosphine)palladium (II) chloride (1.0 g) and triethylamine (6 ml) were dissolved in tetrahydrofuran (200 ml) and heated to 80° C. in a Parr apparatus under an atmosphere of carbon monoxide gas at 1380 kPa (200 psi). After 6 days, the mixture was allowed to cool to ambient temperature and concentrated in vacuo. It was basified to pH14 using 1M sodium hydroxide solution and extracted with ethyl acetate (2×200 ml). These extracts were back extracted with 1M sodium hydroxide solution (2×100 ml) and the combined aqueous phases acidified to pH5 using glacial acetic acid. Ethyl acetate (2×200 ml) extracts of this acidic aqueous phase were washed with water (100 ml) and saturated brine (50 ml) then dried over anhydrous magnesium sulphate, filtered and evaporated in vacuo to afford the title compound as a solid (0.19 g).

TLC $R_f$ 0.20 (ethyl acetate)

INTERMEDIATE 5

4-Methoxy-2-trifluoromethylbenzimidazole

A solution of 2,3-diaminoanisole (1.0 g) in trifluoroacetic acid (15 ml) was refluxed for 5 h and then stirred at room temperature overnight. Excess trifluoroacetic acid was removed in vacuo and the residue partitioned between ethyl acetate (50 ml) and water (50 ml). The organic phase was washed with saturated sodium bicarbonate solution (50 ml) and water (50 ml). Drying over anhydrous sodium sulfate and removal of the solvent in vacuo gave a brown residue. Purification by column chromatography eluting with 50% ethyl acetate in hexane gave the title compound as a yellow solid (1.4 g).

TLC $R_f$ 0.64 (50% ethyl acetate in hexane)

INTERMEDIATE 6

2-(1-Hydroxyethyl)-4-methoxybenzimidazole 2,3-Diaminoanisole (5.88 g) and lactic acid (5.6 ml) were combined, treated with concentrated hydrochloric acid (45 ml) and heated at 100° C. for 18 h. The reaction was cooled to 0° C., neutralised with ammonium hydroxide solution and extracted with ethyl acetate (3×45 ml). The combined organic layers were dried over magnesium sulphate, filtered and the filtrate evaporated in vacuo and the residue purified by flash chromatography on silica eluting with ethyl acetate to yield the desired product as a reddish-brown solid (4.91 g).

TLC $R_f$ 0.125 (ethyl acetate)

INTERMEDIATE 7

2-Acetyl-4-methoxybenzimidazole

A solution of 2-(1-hydroxyethyl)-4-methoxybenzimidazole (2.18 g) in acetic acid (8.5 ml) was heated at 100° C. and treated with a solution of chromium trioxide (0.85 g) in water (3 ml). After 10 minutes the reaction was poured into water (110 ml), the precipitate was removed by filtration through a plug of Celite and the product extracted with dichloromethane (3×100 ml). The combined organic layers were dried over magnesium sulphate, filtered, and evaporated in vacuo and to yield the desired product as a light-brown solid (1.4 g).

TLC $R_f$ 0.6 (ethyl acetate)

INTERMEDIATE 8

7-Methoxy-3-methyl-2-trifluoromethylbenzimidazole

To a solution of 4-methoxy-2-trifluoromethylbenzimidazole (1.4 g) in tetrahydrofuran (40 ml) under nitrogen was added sodium hydride (0.32 g; 60% dispersion in oil). The mixture was stirred for 20 minutes at room temperature before methyl iodide (1.35 g) was added. Stirring was continued overnight. The reaction was quenched by the addition of water (10 ml) and the solvent removed in vacuo. Ethyl acetate (50 ml) was added and the organic layer washed with saturated sodium bicarbonate solution (20 ml), water (20 ml) and brine (20 ml). Drying over anhydrous magnesium sulfate followed by the removal of the solvent in vacuo gave the title compound (1.6 g) as an oil which solidified on standing.

TLC $R_f$ 0.75 (50% ethyl acetate in hexane)

The following compounds were prepared by a similar procedure.

INTERMEDIATE 9

2-Acetyl-7-methoxy-3-methylbenzimidazole

Prepared from 2-acetyl-7-methoxybenzimidazole (0.5 g). Purification by flash chromatography on silica eluting with 50% ethyl acetate in hexane gave the title compound as a white solid (0.24 g).

TLC $R_f$ 0.38 (50% ethyl acetate in hexane)

INTERMEDIATE 10

7-Methoxy-3-propyl-2-trifluoromethylbenzimidazole

Prepared from 4-methoxy-2-trifluoromethylbenzimidazole (2.4 g) and propyl bromide (3.02 ml). Purification by flash chromatography on silica eluting with 15% ethyl acetate in hexane gave the title compound as a white solid (2.03 g).

TLC $R_f$ 0.4 (20% ethyl acetate in hexane)

INTERMEDIATE 11

4-Bromo-7-methoxy-3-methyl-2-trifluoromethylbenzimidazole

To a solution of 7-methoxy-3-methyl-2-trifluoromethylbenzimidazole (1.4 g) in chloroform (50 ml) under nitrogen was added N-bromosuccinimide (1.2 g). The mixture was stirred for 20 minutes before the reaction was quenched by the addition of 5% sodium metabisulphite solution (50 ml) and the organic layer was separated. Washing with water (50 ml), drying over anhydrous magnesium sulphate and removal of the solvent in vacuo gave an orange oil. Purification by flash chromatography eluting with 50% ethyl acetate in hexane gave the title compound as an orange solid (1.73 g).

TLC $R_f$ 0.79 (50% ethyl acetate in hexane)

The following compounds were prepared by a similar procedure.

INTERMEDIATE 12

2-Acetyl-4-bromo-7-methoxy-3-methylbenzimidazole

Prepared from 2-acetyl-7-methoxy-3-methylbenzimidazole (0.24 g). Purification by flash chromatography on silica eluting with 50% ethyl acetate in hexane gave the desired product as a white solid (0.23 g).

TLC $R_f$ 0.5 (50% ethyl acetate in hexane)

INTERMEDIATE 13

4-Bromo-7-methoxy-3-propyl-2-trifluoromethylbenzimidazole

Prepared from 7-methoxy-3-propyl-2-trifluoromethylbenzimidazole (2.03 g). Purification by flash chromatography on silica eluting with 15% ethyl acetate in hexane gave the title compound as a white solid (0.69 g).

TLC $R_f$ 0.4 (20% ethyl acetate in hexane)

INTERMEDIATE 14

7-Methoxy-3-methyl-2-trifluoromethylbenzimidazole-4-carboxylic acid

A mixture of 4-bromo-7-methoxy-3-methyl-2-trifluoromethylbenzimidazole (1.7 g), bis(triphenylphosphine)palladium (II) chloride (0.26 g), triphenylphosphine (0.48 g) and triethylamine (7.7 ml) in tetrahydrofuran (30 ml) and water (10 ml) were heated to 80° C. in a Parr apparatus under an atmosphere of carbon monoxide gas at 1240 kPa (180 psi). After 3 days, the mixture was allowed to cool to ambient temperature and concentrated in vacuo. It was basified to pH14 using 1M sodium hydroxide solution and extracted with ethyl acetate (2×50 ml). The aqueous phase acidified to pH5 using glacial acetic acid. The resulting precipitate was filtered off and washed with water to give the title compound (0.81 g) as an off white solid.

TLC $R_f$ 0.37 (50% ethyl acetate in hexane)

The following compounds were prepared by a similar procedure.

INTERMEDIATE 15

2-Acetyl-7-methoxy-3-methylbenzimidazole-4-carboxylic acid

Prepared from 2-acetyl-4-bromo-7-methoxy-3-methylbenzimidazole. Purification by flash chromatography on silica eluting with 50% ethyl acetate in hexane gave the desired product as a white solid (1.38 g).

TLC $R_f$ 0.75 (50% ethyl acetate in hexane)

INTERMEDIATE 16

7-Methoxy-3-propyl-2-trifluoromethylbenzimidazole-4-carboxylic acid

Prepared from 4-bromo-7-methoxy-3-propyl-2-trifluoromethylbenzimidazole (0.69 g). Trituration with t-butyl methyl ether gave the title compound as a white solid (0.29 g).

TLC $R_f$ 0.4 (50% ethyl acetate in hexane)

INTERMEDIATE 17

4-Bromo-7-methoxy-2-trifluoromethylbenzimidazole

A solution of 7-methoxy-2-trifluoromethylbenzimidazole (50 g) in chloroform (100 ml) was cooled to 0° C., and N-bromosuccinimide (4.5 g) added. The mixture was stirred for 2 h. It was then washed with 5% aqueous sodium metabisulphite (50 ml), dried over magnesium sulphate, evaporated in vacuo and purified by flash chromatography eluting with 25% ethyl acetate in hexane to yield the title compound as a white solid (1.0 g).

TLC $R_f$ 0.29 (20% ethyl acetate in hexane)

INTERMEDIATE 18

4-Bromo-7-methoxy-3-(4-methoxybenzyl)-2-trifluoromethylbenzimidazole

Sodium hydride (0.16 g; 60% dispersion in oil) was added to a solution of 4-bromo-7-methoxy-2-trifluoromethylbenzimidazole (1.0 g) in N,N-dimethylformamide (20 ml). The mixture was stirred at room temperature for 10 minutes before addition of 4-methoxybenzyl chloride (0.56 ml) and catalytic tetrabutylammonium iodide. The reaction was heated at 90° C. for 6 h, then poured into water (100 ml) and extracted with ethyl acetate (2×100 ml). The combined organic phases were washed with water (100 ml) and brine (50 ml), dried over magnesium sulphate, evaporated in vacuo and purified by flash chromatography eluting with 33% ethyl acetate in hexane to afford the title compound as a white solid (0.52 g).

TLC $R_f$ 0.31 (20% ethyl acetate in hexane)

INTERMEDIATE 19

7-Methoxy-3-(4-methoxybenzyl)-2-trifluoromethyl-benzimidazole-4-carboxylic acid A mixture of 4-bromo-7-methoxy-3-(4-methoxybenzyl)-2-trifluoromethyl-benzimidazole (520 mg), bis(triphenylphosphine)palladium (II) chloride (90 mg), triphenylphosphine (100 mg) and triethylamine (1.8 ml) in tetrahydrofuran (50 ml) and water (15 ml) were heated to 80° C. in a Parr apparatus under an atmosphere of carbon monoxide gas at 1240 kPa (180 psi). After 5 days, the mixture was allowed to cool to ambient temperature and concentrated in vacuo. It was basified with 1M sodium hydroxide solution and extracted with ethyl acetate (2×50 ml). The aqueous phase was acidified to pH6 using glacial acetic acid and extracted with ethyl acetate (2×75 ml). The combined extracts were dried over magnesium sulphate and evaporated in vacuo to give the title compound as a cream solid (310 mg).

TLC $R_f$ 0.12 (50% ethyl acetate in hexane)

INTERMEDIATE 20

2-Ethyl-4-hydroxybenzoxazole

A mixture of 2-aminoresorcinol hydrochloride (5.0 g) and triethylorthopropionate (13.7 ml) was heated to 150° C. for 2 h before being poured into a mixture of water (140 ml) and ethanol (35 ml). The mixture was stirred vigorously for 30 minutes at room temperature. The resulting precipitate was removed by filtration and dried to give the title compound as a beige solid (4.11 g).

TLC $R_f$ 0.40 (50% ethyl acetate in hexane)

INTERMEDIATE 21

4-Hydroxybenzoxazole

2-Aminoresorcinol hydrochloride (2 g) and triethylchloroformate (4.5 ml) were heated to reflux under nitrogen for 3 h. After cooling to room temperature, the reaction mixture was poured into a mixture of water (70 ml) and ethanol (20 ml). The mixture was stirred vigorously for 30 minutes, then left to stand at room temperature overnight. The beige precipitate which formed was collected by filtration, and dried by azeotroping with toluene to give the title compound as a beige solid (1.2 g).

INTERMEDIATE 22

2-Ethyl-4-methoxybenzoxazole

2-Ethyl-4-hydroxybenzoxazole (4.17 g) was dissolved in tetrahydrofuran (73 ml) at room temperature. Tetrabutylammonium iodide (0.4 g) was added, followed by a solution of sodium hydroxide (3.89 g) in water (40 ml). The mixture was stirred for 10 minutes before addition of iodomethane (3.13 ml). Stirring was then continued overnight. The crude mixture was evaporated onto silica, and purified by flash chromatography eluting with 25% then 50% ethyl acetate in hexane to give the title compound as a straw coloured liquid (3.05 g).

TLC $R_f$ 0.50 (50% ethyl acetate in hexane)

The following compound was prepared by a similar procedure.

INTERMEDIATE 23

4-Methoxybenzoxazole

Prepared from 4-hydroxybenzoxazole to furnish the title compound (90 mg) as a brown solid.

TLC $R_f$ 0.41 (50% ethyl acetate in hexane)

INTERMEDIATE 24

2-(1-Hydroxyethyl)-4-methoxybenzoxazole

4-Methoxybenzoxazole (6.0 g) was dissolved in tetrahydrofuran (225 ml) and cooled to −78° C. under nitrogen. n-Butyllithium (26.5 ml of a 1.6M solution in hexanes) was added, and the mixture stirred at −78° C. for 30 minutes before addition of magnesium bromide etherate (11.5 g). The resulting heterogeneous mixture was stirred at −45° C. for 15 minutes, and then cooled to −78° C. A solution of acetaldehyde (2.3 ml) was added from a pre-cooled syringe. The mixture was stirred at −78° C. for 3 h, then allowed to warm to room temperature and stirred overnight. It was quenched with aqueous sodium bicarbonate (50 ml, gradually) and the tetrahydrofuran evaporated in vacuo. The residue was extracted with dichloromethane (3×150 ml). The combined organic phases were dried over magnesium sulphate, evaporated in vacuo and purified by flash chromatography eluting with 30%–50% ethyl acetate in hexane to afford the title compound as a brown solid (6.25 g).

TLC $R_f$ 0.14 (30% ethyl acetate in hexane)

INTERMEDIATE 25

2-Acetyl-4-methoxybenzoxazole

A solution of oxalyl chloride (0.25 ml) in dichloromethane (6.5 ml) was cooled to −55° C. under nitrogen. A solution of dimethylsulphoxide (0.44 ml) in dichloromethane (1.3 ml) was added dropwise, and the mixture stirred for 5 minutes at −55° C. before addition of a solution of 2-(1-hydroxyethyl)-4-methoxybenzoxazole (0.5 g) in dichloromethane (2.5 ml). Stirring was continued for 15 minutes at −55° C., then triethylamine (1.8 ml) was added. The mixture was stirred at −55° C. for 5 minutes and was then allowed to warm to room temperature. It was poured into water (25 ml) and the layers separated. The aqueous phase was extracted with dichloromethane (20 ml). The combined organic phases were dried over magnesium sulphate, evaporated in vacuo and purified by flash chromatography eluting with 30% ethyl acetate in hexane to yield the title compound as a white solid (350 mg).

TLC $R_f$ 0.45 (50% ethyl acetate in hexane)

INTERMEDIATE 26

4-Methoxy-2-(2-methyl-[1,3]-dioxolan-2-yl) benzoxazole

2-Acetyl-4-methoxybenzoxazole (200 mg), p-toluenesulphonic acid (239 mg), ethylene glycol (0.29 ml) and toluene (10 ml) were heated to reflux under Dean-Stark conditions for 2 h. After cooling to room temperature, the toluene was evaporated, and the residue partitoned between water (20 ml) and ethyl acetate (20 ml). The aqueous phase was extracted with ethyl acetate (20 ml). The combined organic phases were washed with water (40 ml), aqueous sodium bicarbonate (2×40 ml) and water (40 ml), dried over magnesium sulphate, evaporated in vacuo and purified by flash chromatography eluting with 30% ethyl acetate in hexane to yield the title compound as a white solid (129 mg).

TLC $R_f$ 0.32 (30% ethyl acetate in hexane)

INTERMEDIATE 27

7-Bromo-2-ethyl-4-methoxybenzoxazole

2-Ethyl-4-methoxybenzoxazole (2.81 g) was dissolved in methanol (80 ml) under nitrogen and the solution cooled to −78° C. Bromine (0.73 ml) was added dropwise. The mixture was allowed to warm gradually to room temperature and stirred for 3.5 h. The methanol was evaporated in vacuo and the residue partitioned between ethyl acetate and aqueous sodium bicarbonate. The combined organic phases were washed with 5% aqueous sodium metabisulphite, evaporated onto silica and purified by flash chromatography eluting with 25%–50% ethyl acetate in hexane to give a mixture of the title compound and 2-ethyl-4-methoxybenzoxazole as a pale yellow liquid (2.28 g).

TLC $R_f$ 0.50 (50% ethyl acetate in hexane)

INTERMEDIATE 28

2-Ethyl-4-methoxybenzoxazole-7-carboxylic acid

A mixture of 7-bromo-2-ethyl-4-methoxybenzoxazole (0.7 g), triphenylphosphine (0.273 g) bis(triphenylphosphine)palladium(II)chloride (0.125 g) and triethylamine (3.9 ml) in tetrahydrofuran (19 ml) and water (6.2 ml) were heated to 80° C. in a Parr apparatus under an atmosphere of carbon monoxide gas at 140 psi for 3 days. The mixture was then allowed to cool to ambient temperature and concentrated in vacuo. It was basified to pH14 using 1M sodium hydroxide solution and extracted with ethyl acetate (2×50 ml). The aqueous phase was acidified to pH5 using glacial acetic acid and extracted with dichloromethane. The combined dichloromethane extracts were dried (MgSO$_4$) and evaporated in vacuo to give the title compound as a beige solid (0.40 g).

TLC $R_f$ 0.30 (50% ethyl acetate in hexane)

INTERMEDIATE 29

7-Bromo-4-methoxy-2-(2-methyl-[1,3]-dioxolan-2-yl)benzoxazole

4-Methoxy-2-(2-methyl-[1,3]-dioxolan-2-yl)benzoxazole (129 m), N-bromosuccinimide (107 mg) and acetonitrile (5 ml) were combined and stirred at room temperature under nitrogen for 4 h. The mixture was partitioned between water (20 ml) and ethyl acetate (20 ml). The aqueous phase was extracted with ethyl acetate (20 ml). The combined organic phases were washed with water (2×50 ml), dried over magnesium sulphate, evaporated in vacuo and purified by flash chromatography eluting with 30% ethyl acetate in hexane to yield the title compound as a white solid (95 mg).

TLC $R_f$ 0.41 (30% ethyl acetate in hexane)

The following compound was prepared by a similar procedure.

INTERMEDIATE 30

7-Bromo-4-methoxybenzoxazole

Prepared from 4-methoxybenzoxazole to afford the title compound (635 mg).

TLC $R_f$ 0.51 (30% ethyl acetate in hexane)

INTERMEDIATE 31

4-Methoxy-2-(2-methyl-[1,3]-dioxolan-2-yl) benzoxazole-7-carboxylic acid

7-Bromo-4-methoxy-2-(2-methyl-[1,3]-dioxolan-2-yl) benzoxazole (480 mg), palladium acetate (34 mg), 1,3-bis(diphenylphosphino)propane (126 mg), triethylamine (0.21 ml), water (15 ml) and tetrahydrofuran (30 ml) were combined and heated to 90° C. in a Parr apparatus under 1035 kPa (150 psi) of carbon monoxide for 3 days. After cooling to room temperature, the tetrahydrofuran was evaporated in vacuo. The residue was partitioned between ethyl acetate (50 ml) and water (50 ml). The aqueous layer was extracted with ethyl acetate (50 ml). The combined organic extracts were dried over magnesium sulphate, evaporated in vacuo and purified by flash chromatography eluting with ethyl acetate to yield the title compound as a white solid (190 mg).

TLC $R_f$ 0.51 (ethyl acetate)

INTERMEDIATE 32

4-Methoxybenzoxazole-7-carboxylic acid

7-Bromo-4-methoxybenzoxazole (630 mg), triethylamine (3.85 ml), triphenylphosphine (290 mg), bis(triphenylphosphine)palladium chloride (88 mg), water (20 ml) and tetrahydrofuran (40 ml) were combined and heated to 90° C. in a Parr apparatus under 1035 kPa (150 psi) of carbon monoxide for 3 days. After cooling to room temperature, the tetrahydrofuran was evaporated. The residue was partitioned between ethyl acetate (50 ml) and water (50 ml). The aqueous phase was acidified to pH4 with acetic acid, and the layers separated. The aqueous phase was extracted with ethyl acetate (2×30 ml) followed by dichloromethane (2×30 ml). The combined organic phases were dried over magnesium sulphate and evaporated in vacuo. Purification of the residue by flash chromatography eluting with ethyl acetate and trituration with diethyl ether afforded the title compound as a white solid (125 mg). On standing, a white solid precipitated in the water layer which was removed by filtration and dried in vacuo at 45° C. for 1 hour to give a further portion of the title compound as a white solid (49 mg).

TLC $R_f$ 0.50 (ethyl acetate)

EXAMPLE 1

8-Methoxyquinoxaline-5-[N-(3,5-dichloropyrid-4-yl)]carboxamide

8-Methoxyquinoxaline-5-carboxylic acid (0.19 g) dissolved in dichloromethane (16 ml) under an inert atmosphere was treated with oxalyl chloride (0.3 ml) then 2 drops of N,N-dimethylformamide and stirred at ambient temperature overnight. The reaction mixture was evaporated in vacuo and azeotroped with dry toluene (2×15 ml) to afford the acid chloride dihydrochloride as a brown solid (0.3 g). A solution of this solid in dry N,N-dimethylformamide (10 ml) was added at 60° C. to a mixture of 4-amino-3,5-dichloropyridine (0.16 g), sodium hydride (0.15 g; 60% dispersion in oil) and N,N-dimethylformamide (10 ml) that had already been stirred at ambient temperature for 1 h. After 2 h the mixture was allowed to cool overnight before evaporating in vacuo. The residue was filtered through a pad of silica using hot ethyl acetate and the filtrate evaporated in vacuo to yield another residue. This was purified by column chromatography using 10% methanol in ethyl acetate as eluant to afford the title compound as an off-white solid (0.09 g).

TLC $R_f$ 0.65 (10% methanol in ethyl acetate); mp 205–208° C.

The following compound was prepared by a similar procedure.

EXAMPLE 2

2-Acetyl-7-methoxy-3-methylbenzimidazole-4-[N-(pyridin-4-yl)]carboxamide

Prepared from 2-acetyl-7-methoxy-3-methylbenzimidazole-4-carboxylic acid (0.50 g) and 4-aminopyridine (0.18 g). Purification by flash chromatography on silica eluting with 10% methanol in ethyl acetate gave the title compound as an off-white solid (0.10 g).

TLC $R_f$ 0.31 (10% methanol in ethyl acetate); mp 274–275° C.

EXAMPLE 3

7-Methoxy-3-methyl-2-trifluoromethylbenzimidazole-4-[N-(3,5-dichloropyrid-4-yl)]carboxamide 7-Methoxy-3-methyl-2-trifluoromethylbenzimidazole-4-carboxylic acid (0.40 g) dissolved in dichloromethane (20 ml) under nitrogen was treated with oxalyl chloride (0.28 ml) then 2 drops of N,N-dimethylformamide and stirred at ambient temperature overnight. The reaction mixture was evaporated in vacuo to afford the acid chloride hydrochloride as a brown solid. A solution of this solid in dry N,N-dimethylformamide (10 ml) was added at ambient temperature to a mixture of 4-amino-3,5-dichloropyridine (0.29 g), sodium hydride (0.30 g; 60% dispersion) and N,N-dimethylformamide (10 ml) that had already been stirred at ambient temperature for 1 h. After 2 h the mixture was allowed to cool overnight before evaporating in vacuo. The residue was purified by column chromatography using 50% ethyl acetate in hexane as eluant to afford the title compound as a white solid (0.16 g).

TLC $R_f$ 0.34 (50% ethyl acetate in hexane); mp 228–229° C.

The following compounds were prepared in a similar manner.

EXAMPLE 4

7-Methoxy-3-propyl-2-trifluoromethylbenzimidazole-4-[N-(3,5-dichloropyridin-4-yl)]carboxamide Prepared from 7-methoxy-3-propyl-2-trifluoromethylbenzimidazole-4-carboxylic acid (0.28 g) and 4-amino-3,5-dichloropyridine (0.18 g). Purification by flash chromatography on silica eluting with 40% ethyl acetate in hexane gave the title compound as a white solid (0.006 g).

TLC $R_f$ 0.21 (40% ethyl acetate in hexane); mp 246–247° C.

EXAMPLE 5

2-Acetyl-7-methoxy-3-methylbenzimidazole-4-[N-(3,5-dichloropyrid-4-yl)]carboxamide Prepared from 2-acetyl-7-methoxy-3-methylbenzimidazole-4-carboxylic acid (1.38 g). Purification by flash chromatography eluting with 10% methanol in dichloromethane yielded the title compound (0.75 g) as a beige solid.

TLC $R_f$ 0.5 (10% methanol in dichloromethane); m.p. 290–291° C.

EXAMPLE 6

2-Ethyl-4-methoxybenzoxazole-7-[N-(4-pyridyl)]carboxamide

Oxalyl chloride (0.32 ml) was added to a solution of 2-ethyl-4-methoxybenzoxazole-7-carboxylate (0.40 g) in dichloromethane (20 ml) at room temperature under nitrogen. After stirring for 10 minutes, dry N,N-dimethylformamide (2 drops) was added. Stirring was continued overnight to give a yellow solution which was evaporated to dryness in vacuo. The residue was dissolved in dichloromethane (20 ml). Triethylamine (0.53 ml) was added, followed by 4-aminopyridine (0.20 g), and the mixture stirred at room temperature overnight It was evaporated onto silica, and purified by flash chromatography eluting with dichloromethane then 10% methanol in dichloromethane to give the title compound as a tan solid (0.08 g).

TLC $R_f$ 0.45 (10% methanol in ethyl acetate); mp 140–142° C.

EXAMPLE 7

2-Ethyl-4-methoxybenzoxazole-7-[N-(3,5-dichloropyrid-4-yl)]carboxamide

2-Ethyl-4-methoxybenzoxazole-7-carboxylate (1.24 g), 4-dimethylaminopyridine (catalytic), 4-nitrophenol (1.17 g), and 1-ethyl-3-(3-dimethylaminopropyl)carbodiimide hydrochloride (1.6 g) in dichloromethane (60 ml) were stirred at room temperature for 48 h. The mixture was evaporated onto silica and chromatographed, eluting with 50% ethyl acetate in hexane, to yield 4-nitrophenyl 2-ethyl-4-methoxybenzoxazole-7-carboxylate. 4-Amino-3,5-dichloropyridine (0.57 g) was dissolved in N,N-dimethylformamide (20 ml) at room temperature under nitrogen. Sodium hydride (0.20 g, 60% dispersion) was added, and the mixture stirred for 5 h before addition of the 4-nitrophenyl ester (1.2 g) and stirred for a further 18 h. The reaction mixture was evaporated onto silica and and purified by flash chromatography eluting with 50% ethyl acetate in hexane to separate the title compound as a white solid (0.44 g).

TLC $R_f$ 0.20 (50% ethyl acetate in hexane); mass spectrum (CI) [M+H]$^+$ observed.

EXAMPLE 8

2-Ethyl-4-methoxybenzoxazole-7-[N-(3,5-dichloropyridin-4-yl-N-oxide)]carboxamide A solution of 2-ethyl-4-methoxybenzoxazole-7-[N-(3,5-dichloropyridin-4-yl)]carboxamide (0.05 g) in chloroform (10 ml) was treated with 36–40% peracetic acid in acetic acid (0.03 ml) and stirred for 14 days at room temperature. The reaction mixture was partitioned between dichloromethane (20 ml) and water (20 ml) The organic layer was separated, dried over magnesium sulphate, filtered and the filtrate evaporated in vacuo. Purification by flash chromatography on silica eluting with 10% methanol in ethyl acetate gave the desired product as a white solid (0.018 g).

TLC $R_f$ 0.38 (10% methanol in ethyl acetate); mp 201–203° C.

EXAMPLE 9

4-Methoxybenzoxazole-7-[N-(3,5-dichloropyridin-4-yl)]carboxamide

A mixture of 4-methoxybenzoxazole-7-carboxylic acid (0.16 g), dimethylaminopyridine (catalytic) 4-nitrophenol (0.17 g) and 1-ethyl-3-(3-dimethylaminopropyl) carbodiimide hydrochloride (0.17 g) in dichloromethane (30 ml) was stirred at room temperature under nitrogen overnight. The mixture was diluted with dichloromethane (20 ml) and washed with water (2×50 ml). The combined organic phases were dried over magnesium sulphate and evaporated in vacuo to give 4-nitrophenyl 4-methoxybenzoxazole-7-carboxylate. 4-Amino-3,5-dichloropyridine (0.15 g) was dissolved in N,N-dimethylformamide (5 ml) at room temperature under nitrogen. Sodium hydride (40 mg; 60% disopersion in oil) was added, and the mixture stirred for 1 h before addition of the 4-nitrophenyl ester (0.26 g) in N,N-dimethylformamide (20 ml). After stirring for 60 h, the N,N-dimethylformamide was evaporated in vacuo, and the residue partitioned between ethyl acetate (40 ml) and water (40 ml). The combined organic phases were washed with water (2×40 ml), dried over magnesium sulphate, evaporated onto silica and purified by flash chromatography eluting with 50% ethyl acetate in hexane) to yield the title compound as a white solid (51 mg).

TLC $R_f$ 0.19 (50% ethyl acetate in hexane); mp 193–194.5° C.

The following compounds were prepared by a similar procedure.

EXAMPLE 10

7-Methoxy-3-(4-methoxybenzyl)-2-trifluoromethyl-benzimidazol-4-[N-(3,5-dichloropyridin-4-yl)]carboxamide Prepared from 7-methoxy-3-(4-methoxybenzyl)-2-trifluoromethylbenzimidazole-4-carboxylic acid to furnish the title compound (140 mg) as a white solid.

TLC $R_f$ 0.35 (50% ethyl acetate in hexane); mp 184.5–186° C.

EXAMPLE 11

2-(2-Methyl-[1,3]dioxolan-2-yl)-4-methoxybenzoxazole-7-[N-(3,5-dichloropyridin-4-yl)]carboxylate Prepared from 2-(2-methyl-[1,3]dioxolan-2-yl)-4-methoxybenzoxazole-7-carboxylic acid to yield the title compound (58 mg) as a white solid.

TLC $R_f$ 0.61 (ethyl acetate); mp 155–157° C.

EXAMPLE 12

N-(3,5-Dichloropyrid-4-yl)-7-methoxy-2-trifluoromethylbenz-imidazole-4-carboxamide 7-methoxy-3-(4-methoxybenzyl)-2-trifluoromethylbenzimidazole-4-[N-(3,5-dichloropyrid-4-yl)]carboxamide (50 mg) was stirred in trifluoroacetic acid (3 ml) for 2 h at room temperature. Excess trifluoroacetic acid was removed in vacuo, and the residue partitioned between ethyl acetate (25 ml) and aqueous sodium bicarbonate (25 ml). The aqueous phase was extracted with ethyl acetate (25 ml). The combined organic phases were dried over magnesium sulphate and evaporated in vacuo to give a solid which was triturated with diethyl ether to give the title compound as a cream solid (19 mg).

TLC $R_f$ 0.30 (50% ethyl acetate in hexane); mp 300–301° C.

EXAMPLE 13

2-(1-Hydroxyimino)ethyl-7-methoxy-3-methyl-benzimidazole-4-[N-(3,5-dichloropyridyl)]carboxamide A mixture of 2-acetyl-7-methoxy-3-methylbenzimidazole-4-[N-(3,5-dichloropyrid-4-yl)]carboxamide (0.60 g), hydroxylamine hydrochloride (1.05 g) and pyridine (1.22 ml) in toluene (40 ml) was heated at reflux under Dean-Stark conditions for 21 h. The solvent was evaporated in vacuo and the residue was triturated with water and filtered off. The precipitate was dried in vacuo to furnish the title compound (0.57 g) as a beige solid. m.p. 272–273° C.

Mass spectrum [M+H]⁺ observed

EXAMPLE 14

3-Methyl-2-(1-(2-methylthiazol-4-ylmethoxy) iminoethyl)-7-methoxybenzimidazole-4-[N-(3,5-dichloropyrid-4-yl)]carboxamide Sodium hydride (60%, 43 mg) was added to a solution of 2-(1-hydroxyimino)ethyl-7-methoxy-3-methylbenzimidazole-4-[N-(3,5-dichloropyridyl)] carboxamide (200 mg) in dimethylformamide (20 ml) at room temperature under an inert atmosphere. After 1 h, 4-chloromethyl-2-methylthiazole (217 mg) and dimethylformamide (5 mL) were added and stirring was continued at room temperature for 18 h. The reaction was quenched by the addition of water (25 ml) and extracted into ethyl acetate (3×25 ml). The combined organic phases were dried (magnesium sulphate), filtered and evaporated onto silica gel. Purification by flash chromatography eluting with ethyl acetate afforded the title compound (28 mg) as a white solid. m.p. 220–221° C.

Mass spectrum [M+H]⁺ observed

The following compound was prepared in a similar manner.

EXAMPLE 15

3-Methyl-2-[1-(3-dimethylaminopropyloxy) iminoethyl]-7-methoxybenzimidazole-4-[N-(3,5-dichloropyrid-4-yl)carboxamide Prepared using 2-(1-hydroxyimino)ethyl-7-methoxy-3-methylbenzimidazole-4-[N-(3,5-dichloropyridyl)] carboxamide (330 mg) and N,N-dimethylaminopropyl chloride hydrochloride (383 mg). Purification by flash chromatography eluting with 20% methanol in dichloromethane yielded the title compound (96 mg) as an off-white solid.

TLC $R_f$ 0.25 (20% methanol in dichloromethane); m.p. 186–187° C.

Assay Methods

The assays used to confirm the phosphodiesterase IV inhibitory activity of compounds of formula (i) are standard assay procedures as disclosed by Schilling et al, Anal. Biochem. 216:154 (1994) Thompson and Strada, Adv. Cycl. Nucl. Res. 8:119 (1979) and Gristwood and Owen, Br. J. Pharmacol. 87:91P (1986).

Compounds of formula (i) have exhibited activity at levels consistent with those believed to be useful in treating phosphodiesterase IV-related disease states in those assays.

The ability of compounds of formula (i) to inhibit TNF production in human monocytes is measured as follows. Peripheral blood mononuclear cells are prepared from freshly taken blood by standard procedures. Cells are plated out in RPMII640+1% foetal calf serum in the presence and absence of inhibitors, LPS (100 ng/ml) is added and cultures are incubated for 22 h at 37° C. in an atmosphere of 95% air/5% $CO_2$. Supernatnts are tested for TNFα by ELISA using commercially available kits.

In vivo activity in a skin eosinophilia model is determined by using the methods described by Hellewell et al. Br. J. Pharmacol. 111:811 (1994) and Br. J. Pharmacol. 110:416 (1993). Activity in a lung model is measured using the procedures described by Kallos and Kallos, Int. Archs. Allergy Appl. Immunol. 73:77 (1984), and Sanjar et al, Br. J. Pharmacol. 99:679 (1990).

An additional lung model, which allows measurement of inhibition of the early and late-phase asthmatic responses and also the inhibition of airway hyperreactivity, is described by Broadley et al. Pulmonary Pharmacol. 7:311 (1994), J. Immunological Methods 190:51 (1996) and British J. Pharmacol. 116:2351 (1995). Compounds of the invention show activity in this model.

What is claimed is:

1. A compound of the general formula (i)

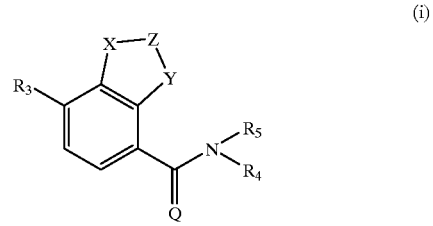

wherein

X is N;

Z is =$CR_1$— and Y is O or S;

Q is selected from the group consisting of O and S;

$R_1$ is selected from the group consisting of $COR_6$, $C(=NOR_6)R_{13}$, alkyl-$C(=NOR_6)R_{13}$, $NR_8R_9$, $CON(R_6)_2$, halogen, $CF_3$, CN, $CO_2H$, $CO_2R_{10}$, $R_6$, CO-het where het is a heterocyclic ring attached via a N atom in the ring and optionally substituted with one or more $R_{14}$, or the cyclic group

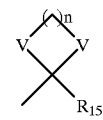

$R_3$ is selected from the group consisting of OH, thioalkyl, and $C_{1-6}$ alkoxy or cycloalkoxy each optionally substituted with one or more halogens;

$R_4$ is selected from the group consisting of H and alkyl;

$R_5$ is aryl or heteroaryl, (or N-oxides thereof) either of which may be optionally substituted with one or more substituents selected from the group consisting of halogen, optionally halogen-substituted alkyl, hydroxy, optionally halogen-substituted alkoxy, $CO_2H$, $CO_2R_{10}$, $CONR_{11}R_{12}$, $COR_{10}$, $SO_2R_{10}$, $SO_2NR_{11}R_{12}$, $NR_8R_9$, and CN;

each $R_6$ is independently selected from the group consisting of H, alkyl, cycloalkyl, aryl, heteroaryl, heterocyclo, arylalkyl, heteroarylalkyl, and heterocycloalkyl, any of which groups is optionally substituted at any position with $R_7$;

$R_7$ is selected from the group consisting of alkyl, hydroxy, $OR_{10}$, $NR_8R_9$, CN, $CO_2H$, $CO_2R_{10}$, $CONR_{11}R_{12}$, and $COR_{10}$;

$R_8$ is selected from the group consisting of H, alkyl, cycloalkyl, aryl, heteroaryl, heterocyclo, arylalkyl, heteroarylalkyl, heterocycloalkyl, alkylcarbonyl, alkoxycarbonyl, arylcarbonyl, heteroarylcarbonyl, heterocyclocarbonyl, alkylsulphonyl, arylsulphonyl, heteroarylsulphonyl, and heterocyclosulphonyl; $R_9$ is selected from the group consisting of H, alkyl, cycloalkyl, aryl, heteroaryl, heterocyclo, aralkyl, heteroarylalkyl, and heterocycloalkyl; or $NR_8R_9$ is a heterocyclic ring optionally substituted with $R_{14}$;

$R_{10}$ is selected from the group consisting of alkyl, cycloalkyl, aryl, heteroaryl, heterocyclo, arylalkyl, heteroarylalkyl, and heterocycloalkyl;

$R_{11}$ and $R_{12}$ are the same or different and are each H or $R_{10}$;

$R_{13}$ is $R_{10}$ optionally substituted with one or more $R_7$;

$R_{14}$ is selected from the group consisting of alkyl, arylalkyl, and heteroarylalkyl; and $R_{15}$ is alkyl; V is O or S, and n=2–4;

or a pharmaceutically-acceptable salt thereof.

2. The compound, according to claim 1, wherein $R_3$ is methoxy.

3. The compound, according to claim 1, wherein $R_4$ is H.

4. The compound, according to claim 2, wherein $R_4$ is H.

5. The compound, according to claim 1, wherein $R_5$ is optionally-substituted 4-pyridyl or optionally-substituted 4-pyridyl-N-oxide.

6. The compound, according to claim 1, wherein $R_1$ is selected from the group consisting of $COR_6$, $C(=NOR_6)R_{13}$, $CF_3$, CN, $R_6$, and said cyclic group.

7. The compound, according to claim 1, wherein $R_1$ is selected from the group consisting of $COR_6$, $C(=NOR_6)R_{13}$, alkyl-$C(=NOR_6)R_{13}$, $NR_8R_9$, $CON(R_{13})_2$, halogen, $CF_3$, CN, $CO_2H$, $CO_2R_{10}$, and $R_6$;

$R_3$ is selected from the group consisting of OH, thioalkyl, and optionally-substituted alkoxy;

$R_5$ is aryl or heteroaryl, either of which may be optionally substituted with one or more substituents selected from the group consisting of halogen, alkyl, hydroxy, alkoxy, $CO_2H$, $CO_2R_{10}$, $CONR_{11}R_{12}$, $COR_{10}$, $SO_2R_{10}$, $SO_2NR_{11}R_{12}$, $NR_8R_9$, and CN;

$R_7$ is not alkyl; and $R_8$ and $R_9$ are independent.

8. The compound, according to claim 7, wherein

Q is O;

$R_1$ is selected from the group consisting of $COR_{13}$, $C(=NOR_{10})R_{13}$, CN, $CO_2H$, $CO_2R_{10}$, $CONR_{11}R_{12}$, and $R_6$;

$R_3$ is $C_{1-6}$ alkoxy optionally substituted with one or more halogens;

$R_6$ is selected from the group consisting of H, alkyl, aryl, heteroaryl, heterocyclo, arylalkyl, heteroarylalkyl, and heterocycloalkyl, any of which groups is optionally substituted at any position with $R_7$;

$R_{10}$ is selected from the group consisting of alkyl, aryl, heteroaryl, heterocyclo, arylalkyl, heteroarylalkyl, and heterocycloalkyl; and $R_{11}$ and $R_{12}$ are the same or different and are each H or $R_{10}$.

9. The compound, according to claim 1, selected from the group consisting of 2-ethyl-4-methoxybenzoxazole-7-[N-(4-pyridyl)]carboxamide; and 2-ethyl-4-methoxybenzoxazole-7-[N-(3,5-dichloropyrid-4-yl)]carboxamide.

10. The compound, according to claim 1, selected from the group consisting of 2-ethyl-4-methoxybenzoxazole-7-[N-(3,5-dichloropyrid-4-yl)]carboxamide;

2-ethyl-7-methoxybenzoxazole-4-[N-(3,5-dichloropyridin-4-yl-N-oxide)]carboxamide;

4-methoxybenzoxazole-7-[N-(3,5-dichloropyridin-4-yl)]carboxamide; and 2-(2-methyl-[1,3]dioxolan-2-yl)-4-methoxybenzoxazole-7-[N-(3,5-dichloropyridin-4-yl)]carboxamide.

11. The compound, according to claim 1, wherein said compound is in the form of an enantiomer.

12. A pharmaceutical composition for therapeutic use comprising a compound of claim 1 and a pharmaceutically-acceptable carrier or excipient.

13. A method for treating a disease state capable of being modulated by inhibition of phosphodiesterase IV or Tumour Necrosis Factor, or that is a pathological condition associated with a function of phosphodiesterase IV, eosinophil accumulation, or a function of the eosinophil, wherein said method comprises administration to a human or animal in need of such treatment an effective amount of a compound of claim 1.

14. The method, according to claim 13, wherein said disease state is an inflammatory disease or an autoimmune disease.

15. The method, according to claim 13, wherein said disease state is selected from the group consisting of asthma, chronic bronchitis, chronic pulmonary inflammatory disease, chronic obstructive airways disease, atopic dermatitis, allergic rhinitis, psoriasis, arthritis, rheumatoid arthritis, joint inflammation, ulcerative colitis, Crohn's disease, atopic eczema, stroke, bone resorption disease, multiple sclerosis, and inflammatory bowel disease.

16. The method, according to claim 13, wherein said disease state is selected from the group consisting of urticaria, allergic conjunctivitis, vernal conjunctivitis, inflammation of the eye, allergic responses in the eye, eosinophilic granuloma, gouty arthritis and other arthritic conditions, adult respiratory distress syndrome, diabetes insipidus, keratosis, cerebral senility, multi-infarct dementia, senile dementia, memory impairment associated with Parkinson's disease, depression, cardiac arrest, intermittent claudication, rheumatoid spondylitis, osteoarthritis, sepsis, septic shock, endotoxin shock, gram negative sepsis, toxic shock syndrome, cerebral malaria, silicosis, pulmonary sarcoidosis, reperfusion injury, graft vs. host reaction. allograft rejection, infection-related fever or myalgia, malaria, HIV, AIDS, ARC, cachexia, keloid formation, scar tissue formation, pyresis, systemic lupus erythematosus, type I diabetes mellitus, Bechet's disease, anaphylactoid purpura nephritis, chronic glomerulonephritis, leukaemia, tarditive dyskensia, yeast or fungal infection, conditions requiring gastroprotection, and neurogenic inflammatory disease associated with irritation and pain.

17. The method, according to claim 13, wherein said disease state is asthma.

18. The method, according to claim 13, wherein said disease state is selected from the group consisting of chronic obstructive airways disease, chronic bronchitis, and chronic pulmonary inflammatory disease.

* * * * *